(12) United States Patent
Biedermann et al.

(10) Patent No.: US 7,618,458 B2
(45) Date of Patent: Nov. 17, 2009

(54) HEIGHT-ADJUSTABLE INTERVERTEBRAE IMPLANT

(75) Inventors: Lutz Biedermann, VS-Villingen (DE); Wilfried Matthis, Weisweil (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 204 days.

(21) Appl. No.: 11/009,224

(22) Filed: Dec. 9, 2004

(65) Prior Publication Data

US 2005/0125062 A1    Jun. 9, 2005

Related U.S. Application Data

(60) Provisional application No. 60/528,412, filed on Dec. 9, 2003.

(30) Foreign Application Priority Data

Dec. 9, 2003  (DE) ................. 103 57 960

(51) Int. Cl.
A61F 2/44 (2006.01)
(52) U.S. Cl. .................................. 623/17.15
(58) Field of Classification Search .... 623/17.11–17.16
See application file for complete search history.

(56) References Cited

U.S. PATENT DOCUMENTS

| | | | | |
|---|---|---|---|---|
| 5,865,848 | A * | 2/1999 | Baker ...................... | 623/17.15 |
| 6,126,689 | A * | 10/2000 | Brett ....................... | 623/17.16 |
| 6,159,244 | A * | 12/2000 | Suddaby .................. | 623/17.11 |
| 6,176,882 | B1 | 1/2001 | Biedermann et al. | |
| 6,193,757 | B1 * | 2/2001 | Foley et al. .............. | 623/17.16 |
| 6,425,919 | B1 * | 7/2002 | Lambrecht ............... | 623/17.16 |
| 6,491,724 | B1 * | 12/2002 | Ferree ..................... | 623/17.11 |
| 6,524,341 | B2 * | 2/2003 | Lang et al. ............... | 623/17.15 |

(Continued)

FOREIGN PATENT DOCUMENTS

DE    40 12 622 C1    7/1991

(Continued)

OTHER PUBLICATIONS

English Abstract of DE 4012622 (C1) dated Jul. 18, 1991, which was previously submitted on Dec. 9, 2004.

(Continued)

*Primary Examiner*—David J Isabella
*Assistant Examiner*—Ann Schillinger
(74) *Attorney, Agent, or Firm*—Christie, Parker & Hale, LLP

(57) ABSTRACT

An intervertebral implant for insertion between two vertebrae is disclosed. A first part has a first contact surface extending between its two ends a first guide surface extending out from the first contact surface. A second part has a second contact surface extending between its ends, and a second guide surface recessed into the second contact surface. The first guide surface and the second guide surface cooperate so that the first contact surface of the first part can slide relative to the second contact surface of the second part with a translation motion guided by the cooperating structures of the first and second guide surfaces. The height of the intervertebral implant can be altered by shifting the first part and the second part relative to each other by moving the contact surfaces relative to each other by using the cooperating guide surfaces.

17 Claims, 7 Drawing Sheets

U.S. PATENT DOCUMENTS

| | | |
|---|---|---|
| 6,648,917 B2 * | 11/2003 | Gerbec et al. ............ 623/17.11 |
| 6,679,915 B1 * | 1/2004 | Cauthen .................. 623/17.11 |
| 7,044,971 B2 * | 5/2006 | Suddaby .................. 623/17.15 |
| 7,094,257 B2 * | 8/2006 | Mujwid et al. ........... 623/17.15 |
| 2002/0107570 A1 * | 8/2002 | Sybert et al. ............. 623/13.17 |
| 2002/0128716 A1 * | 9/2002 | Cohen et al. ............. 623/17.15 |
| 2003/0171813 A1 * | 9/2003 | Kiester .................... 623/17.11 |
| 2004/0002764 A1 * | 1/2004 | Gainor et al. ............ 623/17.16 |
| 2004/0133281 A1 * | 7/2004 | Khandkar et al. ........ 623/17.16 |
| 2004/0158328 A1 * | 8/2004 | Eisermann ............... 623/17.16 |
| 2005/0107878 A1 | 5/2005 | Conchy |
| 2006/0009850 A1 * | 1/2006 | Frigg et al. .............. 623/17.13 |

FOREIGN PATENT DOCUMENTS

| | | |
|---|---|---|
| EP | 0 977 529 | 2/2000 |
| EP | 0 977 529 B1 | 2/2003 |
| EP | 1 293 180 A1 | 3/2003 |
| FR | 2 817 463 | 6/2002 |
| WO | WO 99/13806 | 3/1999 |
| WO | WO 01/49220 A1 | 7/2001 |
| WO | WO 02/09626 A1 | 2/2002 |
| WO | WO 02/080823 A1 | 10/2002 |
| WO | WO 2004/073563 A2 | 9/2004 |

OTHER PUBLICATIONS

English Abstract of EP1293180 dated Mar. 19, 2003, which was previously submitted on Dec. 9, 2004.

* cited by examiner (A)

(B)

(A)

(B)

(A)

(B)

HEIGHT-ADJUSTABLE INTERVERTEBRAE IMPLANT

CROSS REFERENCE TO RELATED APPLICATIONS

This application claims priority from U.S. Provisional Application Ser. No. 60/528,412 filed Dec. 9, 2003.

FIELD OF THE INVENTION

The present invention relates to intervertebral implants, particularly, to height-adjustable intervertebral implants.

BACKGROUND OF THE INVENTION

Intervertebral implants are employed generally after the removal of an intervertebral disc in order to stabilize the space between the vertebrae.

An intervertebral implant is described in EP 0 977 529 B1. The implant is shaped essentially like a rectangular parallelepiped and comprises two side walls, one front wall, and one back wall. The bottom surface and the top surface are open. The hollow space of the intervertebral implant enclosed by the four walls contains at least one movable element with a surface facing towards the top surface or bottom surface, and one adjustment element that is supported in the front wall and back wall, allowing the movable element to be moved back and forth between a first position, in which its surface does not protrude beyond the top surface or bottom surface, and a second position, in which its surface protrudes beyond the top surface or bottom surface. This movement between the first and second positions allows for the final height of the intervertebral implant to be adjustable.

Moreover, a curved intervertebral implant resembling the shape of a banana and made as one part also is known. However, this known intervertebral implant is not height-adjustable.

Thus, a height-adjustable intervertebral implant remains desirable. The implant should also be particularly well-suited for the use in minimally-invasive applications.

SUMMARY OF THE INVENTION

The present invention provides an intervertebral implant comprising two parts. A first part has a first end, a second end, a first contact surface provided between the ends and a first guide surface extending out from the first contact surface. A second part also has two ends (more specifically referred to as the third and fourth ends), a second contact surface provided therebetween, and a second guide surface recessed into the second contact surface. The first guide surface and the second guide surface have cooperating or mating structures so that the first contact surface of the first part can slide relative to the second contact surface of the second part with a translation motion guided by the cooperating structures of the first and second guide surfaces.

Certain preferred embodiments of an intervertebral implant in accordance with the present invention can have one or more of the following features:

the distance between the first contact surface of the first part and a first base surface that is opposite to the first contact surface is smaller at the first end of the first part than at the second end, and the distance between the second contact surface of the second part and a second base surface that is opposite to the second contact surface is smaller at one end (i.e., the third end) of the second part than the other end (i.e., the fourth end);

the first part comprises a first base surface opposite to said first contact surface, and a first plane parallel to said first contact surface intersects a second plane parallel to said first base surface forming an inclination angle of contact α; and the second part comprises a second base surface opposite to said second contact surface, and a third plane parallel to said second contact surface intersects a fourth plane parallel to said second base surface forming an inclination angle of contact α;

the contact surfaces and the guiding surfaces can be arcuate, curved or shaped like a segment of a helix;

at least one of the contact surfaces includes a terminal stop to prevent further translation of the surfaces;

an inclination angle (α) of the contact surfaces with their respective base surfaces is formed which depends on the material used to form the parts and the surface properties of the two contact surfaces such that a self-locking mechanism results between the first part and the second part;

the guide surfaces are provided with cooperating ridge-and-groove structures;

the first contact surface, the second contact surface, the ridge, and the groove are each arcuate, curved or shaped like a segment of a helix;

the groove terminates at a distance from the distal end of the second contact surface such that a terminal stop is effected for the gliding of the contact surfaces on each other;

the cross-section of the ridge protruding from the first contact surface comprises a shape having a cross section selected from the group comprising a dovetail-shape, a T-shape, a rectangular or a square shape or a semicircular shape, and the groove in the second contact surface comprises a complementary shape for receiving the ridge;

the first part and/or the second part can comprise an orifice or a recess;

the first contact surface and/or the second contact surface comprise a roughened portion or a step-like portion; and the first base surface and/or the second base surface comprise groove-shaped recesses.

The invention also provides a method for stabilizing the space between vertebrae by providing an intervertebral implant as described herein, adjusting the height of the implant by connecting, for example, the second end of the first part with the third end of the second part and moving the first contact surface relative to the second contact surface to bring the first end of the first part closer to the fourth end of the second part using the cooperating guide surfaces, and inserting the adjusted height implant between the vertebrae needing to be stabilized.

Use of an intervertebral implant in accordance with the present invention can enable one to alter the height (or thickness) of the implant in its assembled state by shifting the first part and the second part relative to each other by means of the contact surfaces moving relative to each other. The motion of the first part and the second part relative to each other, preferably proceeding in an arcuate path such as a screw or helical motion, is particularly well-suited for the use of the intervertebral implant in minimally-invasive applications.

In certain preferred embodiments, a terminal stop is provided, which prevents the gliding motion of the first part and the second part relative to each other from proceeding beyond a terminal position.

In other preferred embodiments, a self-locking mechanism such as, for example, roughened or stepped contact surfaces, are provided, which prevents the inadvertent shifting of the first part and the second part relative to each other.

Additional features and expediencies of the present invention are evident from the description of embodiments and the attached drawings.

DETAILED DESCRIPTION OF THE INVENTION

An intervertebral implant according to one embodiment of the present invention is illustrated with reference to FIGS. 1 to 6. As is evident from FIG. 1 and FIG. 2, intervertebral implant 1 consists of two curved parts 10, 20, which are provided to be in the shape of an arc, curve or segment of a helix in this particular embodiment.

Figure 6:
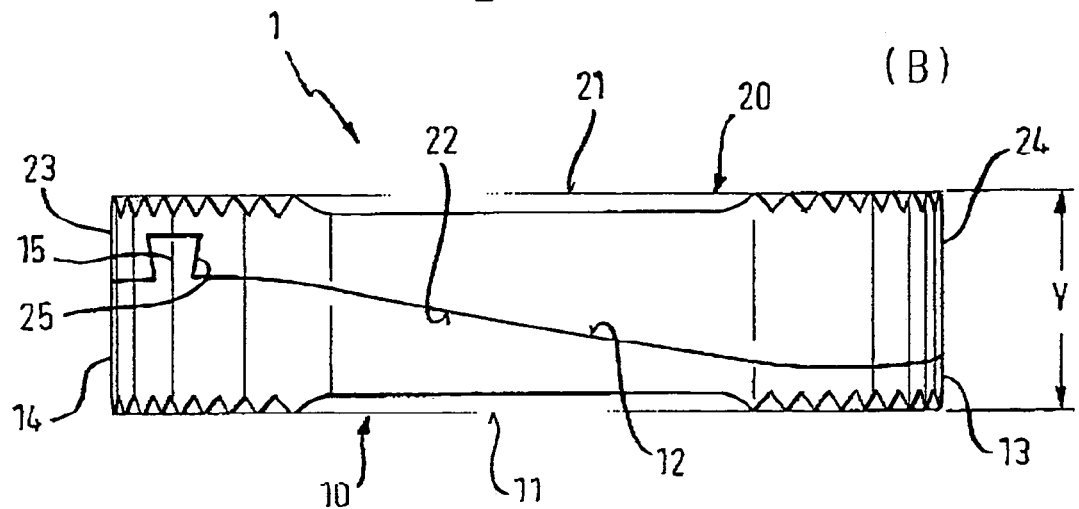
FIG. 6 shows a front elevational view of the intervertebral implant in the state illustrated in FIG. 2.

As is best seen in FIG. 6, the two parts 10, 20 are provided as wedge-like sections with opposite tapers, each of which has a thick end 14, 24 that forms a base end of the wedge and a tapered end 13, 23 opposite to the thick end. In this arrangement, the two parts 10, 20 can be connected together by contacting each other at their wedge surfaces 12, 22 using the guide surfaces provided by ridge 15 and groove 25. Thus, reference generally will be made to these wedge surfaces as "contact surfaces" 12, 22, hereinafter. Thus, seen from an elevational view (such as FIG. 6), when the two parts are fully engaged, intervertebral implant 1 is approximately rectangular in shape. By shifting the two parts 10, 20 relative to each other along their contact surfaces 12, 22, the total height of intervertebral implant 1 can be adjusted.

Figure 1:
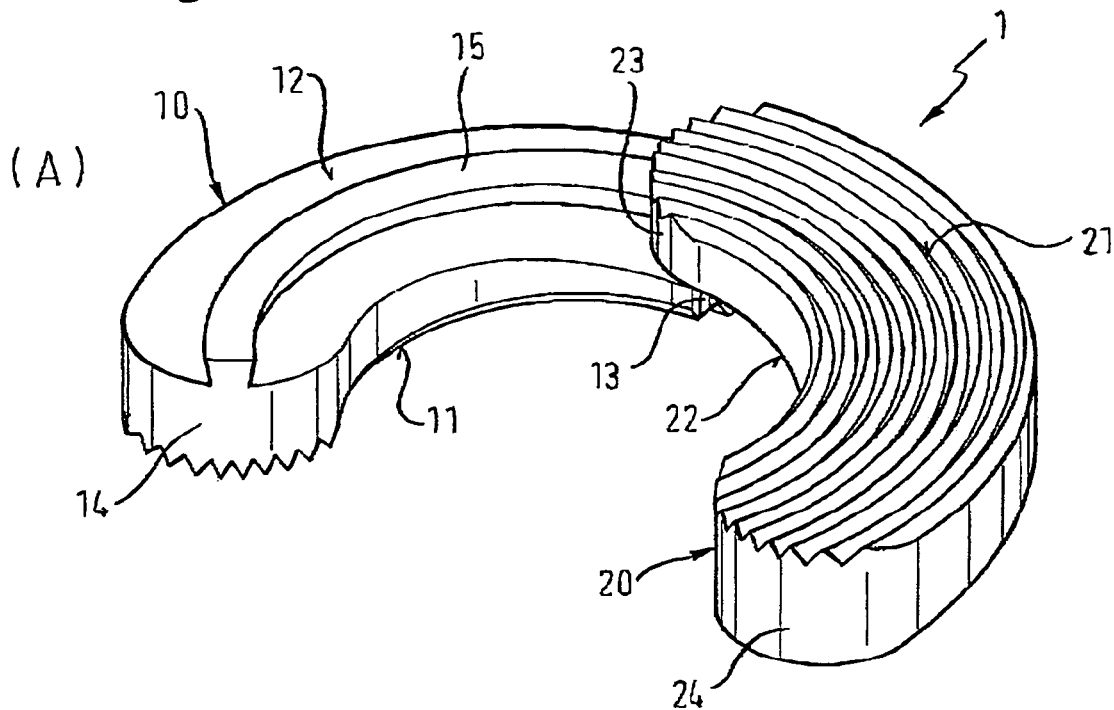
FIG. 1 shows a perspective view of an intervertebral implant according to one embodiment of the present invention in a state in which the two parts are minimally engaged.
Figure 2:
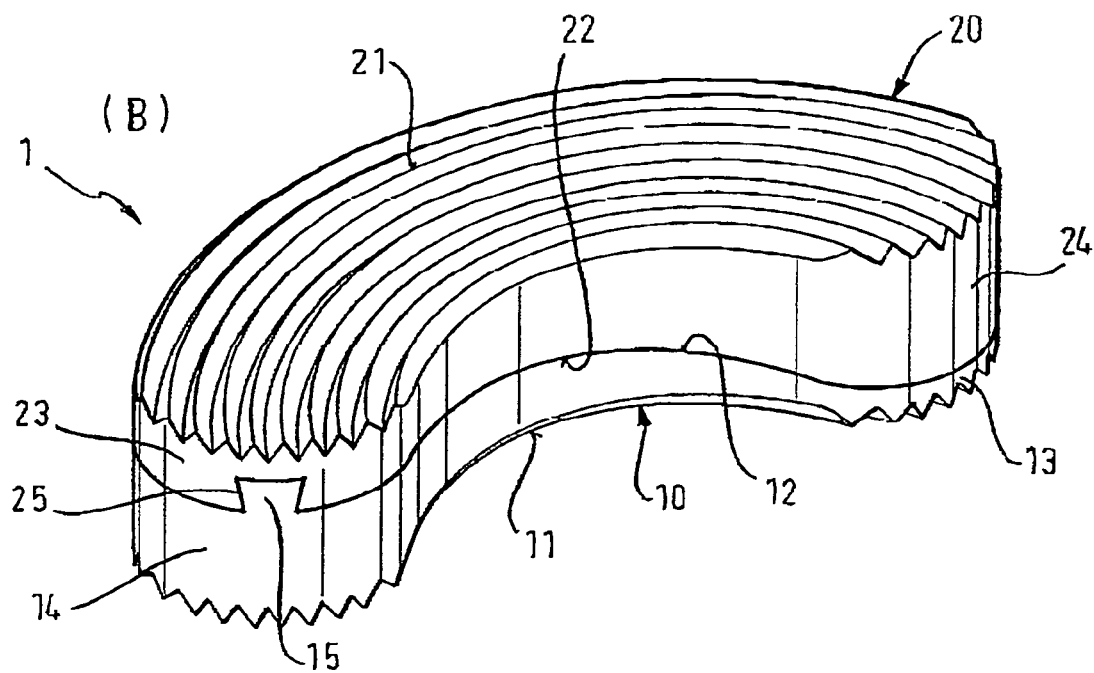
FIG. 2 shows a perspective view of the intervertebral implant depicted in FIG. 1 in a state in the two parts are fully engaged.
Figure 3:
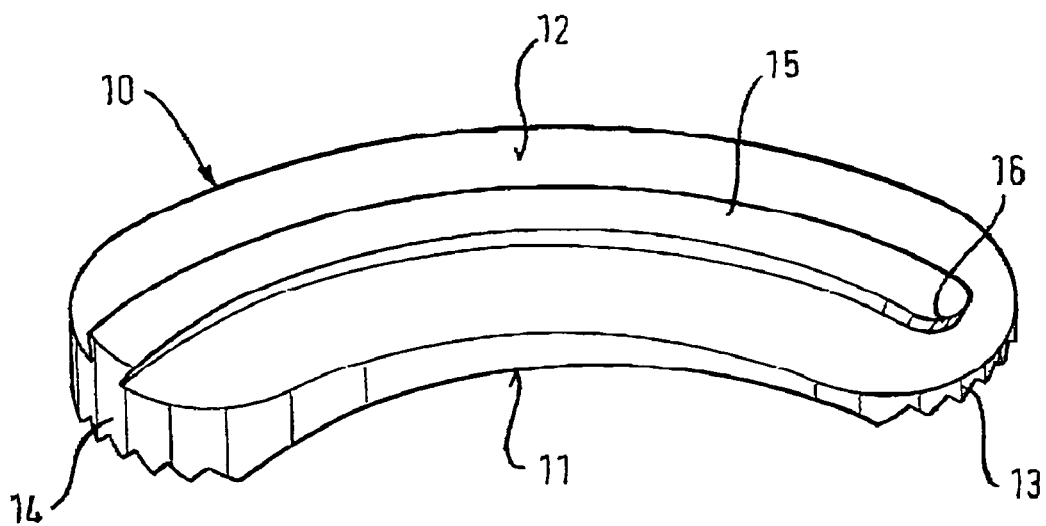
FIG. 3 shows a perspective view of a first part of the intervertebral implant of FIG. 1.

As is best seen in FIG. 3, first part 10 comprises a first contact surface 12 and a first base surface 11 opposite to contact surface 12. First contact surface 12 is provided preferably in the form of a section of an arc, curve or shaped like a segment of a helix. In this embodiment, a ridge 15 with a dovetail-shaped cross-section is provided on first contact surface 12 such that it protrudes at a right angle from the surface (i.e. in a direction perpendicular to the plane of the surface). Ridge 15 can be in the form of an arc, curve or shaped like a segment of a helix. Ridge 15 extends from the second end 14 of first part 10, which forms the base of the wedge, preferably to a distance from the tapered first end 13.

Figure 4:
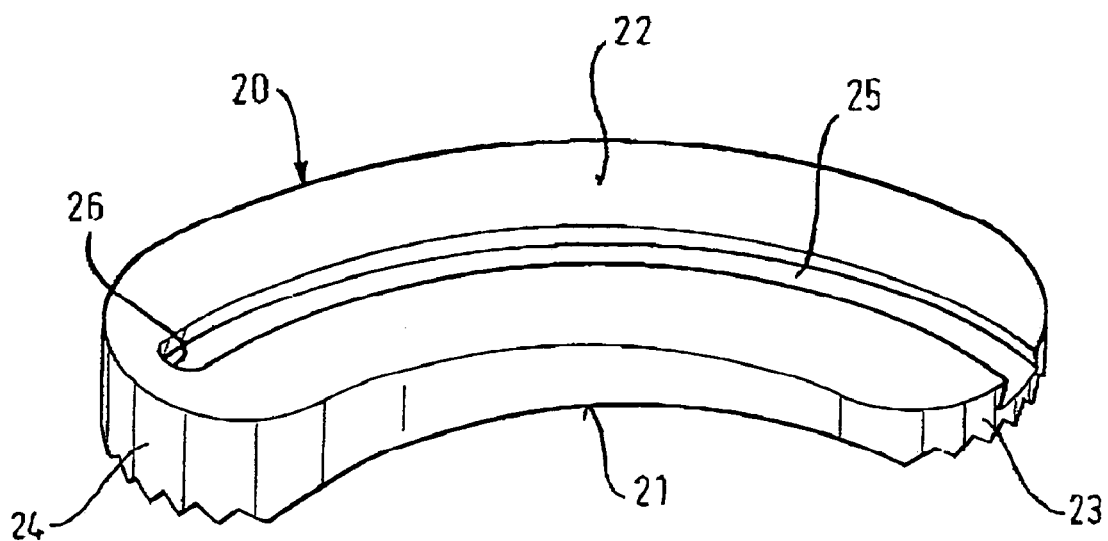
FIG. 4 shows a perspective view of a second part of the intervertebral implant of FIG. 1.

As is best seen in FIG. 4, second part 20 includes a second contact surface 22 and a second base surface 21 opposite to second contact surface 22. Second contact surface 22 also is in the form of an arc, curve or a segment of a helix, provided that it is complementary to that of the first contact surface 12 and matingly cooperates with the first contact surface. A groove 25 with a dovetailed cross-section that corresponds to the cross-section of ridge 15 is provided in second contact surface 22. Groove 25 also is shaped like an arc, curve or segment of a helix. Groove 25 extends from the tapered first end 23 of second part 20 preferably to a distance from the second end 24, which forms the base end of the wedge.

Alternatively to the ridge and groove shown any type of a positive structure protruding from the first contact surface which cooperates with a corresponding negative structure or recess in the second contact surface and which can slide relative to the second contact surface can be used. Positive and negative structures can be interchanged, so that the positive structure is provided on the second contact surface and the negative structure is provided in the first contact surface.

The first base surface 11 and the second base surface 21 may also be provided with groove-shaped recesses, which also are circular arc-shaped in this embodiment when viewed in a top view. Any type or shape of grooved recess may be used in the alternative.

In order to adjust the height of intervertebral implant 1 as desired, first part 10 and second part 20 are shifted relative to each other in a sliding motion along their contact surfaces 12, 22 contacting between a first position A (see FIGS. 1 and 5) and a second position B (see FIGS. 2 and 6), whereby ridge 15 is guided within groove 25. The second position B is reached once ridge end 16 pushes against groove end 26 forming a terminal stop. In this embodiment, groove end 26 prevents the parts from being pushed beyond the terminal stop position.

Figure 5:
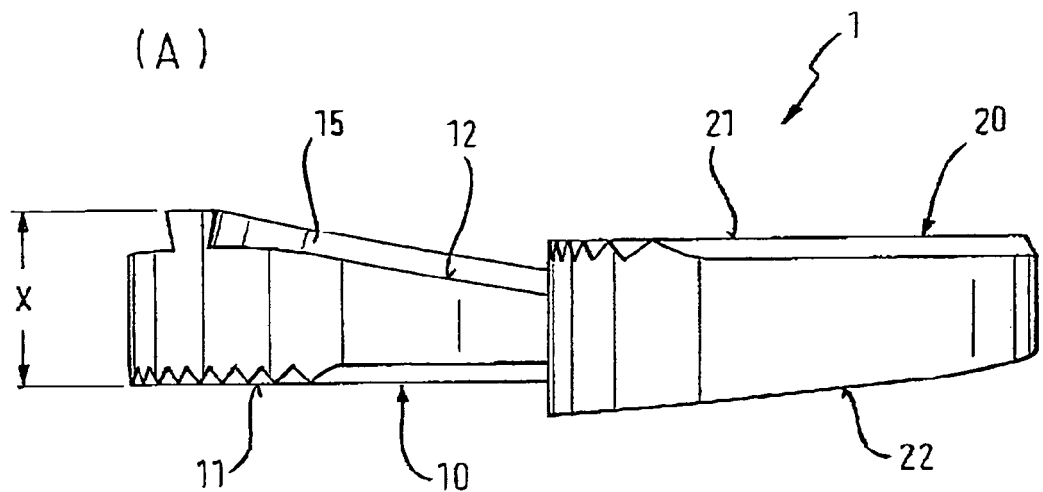
FIG. 5 shows a front elevational view of the intervertebral implant in the state illustrated in FIG. 1.

As is best seen in FIGS. 5 and 6, the inclination of contact surfaces 12, 22 with respect to base surfaces 11, 21 causes intervertebral implant 1, after being pushed together into the second position B to be of a height Y that exceeds the height X in the first position A before the parts are pushed together. Therefore, it is possible to adjust the height of intervertebral implant 1 between the two limits X and Y by means of a gliding motion of first part 10 and second part 20 relative to each other.

In application, for the insertion of intervertebral implant 1 between two vertebrae, the desired height is obtained by moving the first part 10 and second part 20 relative to each other with the contact surfaces and guide surfaces in contact. Once the desired height is obtained the intervertebral implant 1 is inserted between the vertebrae. The vertebrae are then fixed with the implant positioned between them.

Figure 7:
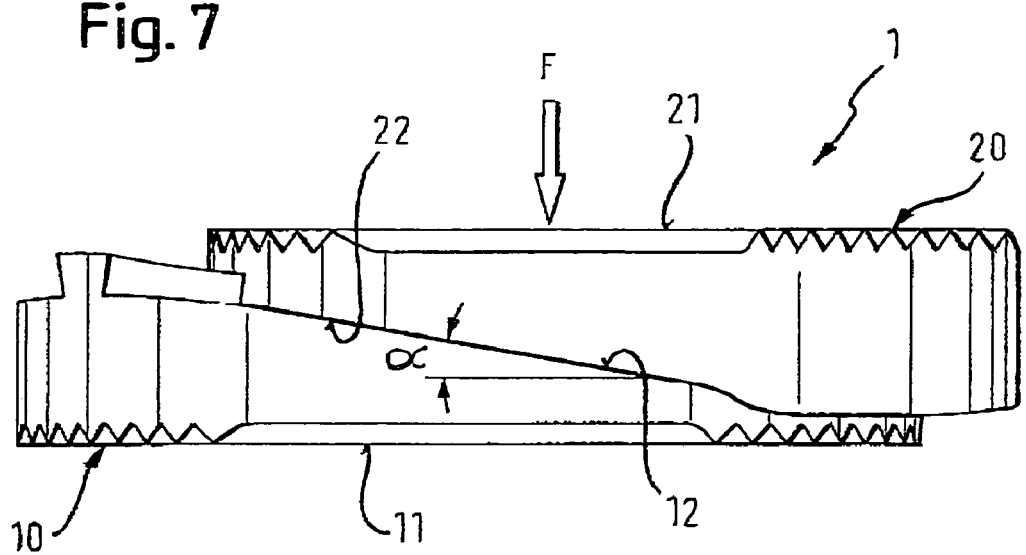
FIG. 7 shows a schematic representation of a self-locking mechanism effected by the acting force F.

FIG. 7 shows a force F acting upon the intervertebral implant 1 after its insertion between the vertebrae. In order to prevent force F from moving the first part 10 inadvertently with respect to the second part 20, the inclination angle α of contact surfaces 12, 22, defining the angle of the contact surface 12, 22 of each part relative to the base surface 11, 21 preferably is determined to result in a self-locking mechanism. The angle is dependent on the material used to form the actual implant and the frictional surface properties of contact surfaces 12, 22 to result in a self-locking mechanism so that the following condition $$\alpha < \rho_o \text{ (whereby } \rho_o = \text{arc tan } \mu_o)$$

is essentially satisfied. In the above equation $\rho_o$ is the friction angle and $\mu_o$ is the static friction coefficient of the material.

Preferably the intervertebral implant is formed from titanium. However, alternatively, other body-compatible metals or alloys or polymer materials including those well known to those skilled in the art can be used. Examples of suitable polymer materials are polyetheretherketone("PEEK") or polytetrafluoroethylene ("PTFE") or. The polymeric material can be reinforced with fibers, including carbon fibers.

Figure 8:
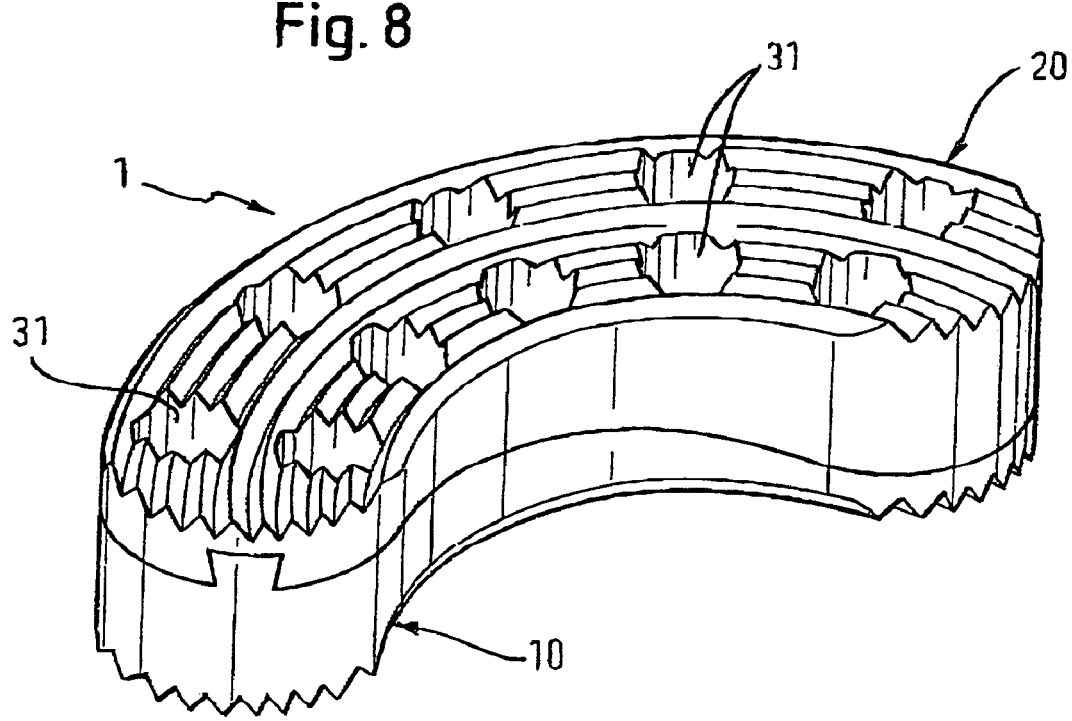
FIG. 8 shows a perspective view of another embodiment of an intervertebral implant in accordance with the present invention.

In the embodiment shown in FIG. 8, the external surfaces of first part 10 and/or second part 20 can include recesses 31 formed as boreholes or orifices. The recessesallow for the in-growth of bone material into intervertebral implant 1.

In yet another embodiment, ridge 15 and groove 25 are provided such that they each extend from first end 13, 23 of the corresponding part 10, 20 to the corresponding second end 14, 24. This arrangement allows the two parts to be shifted relative to each other beyond second position B and, thus, provides for the height in the assembled state to have a larger adjustable range.

Figure 9A:
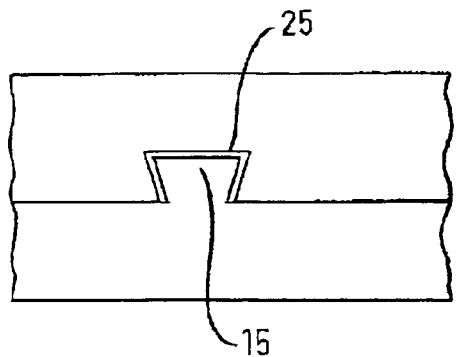
FIG. 9a) to 9e) show different shapes of the mating groove/ridge structure provided at the contact surfaces.
Figure 9B:
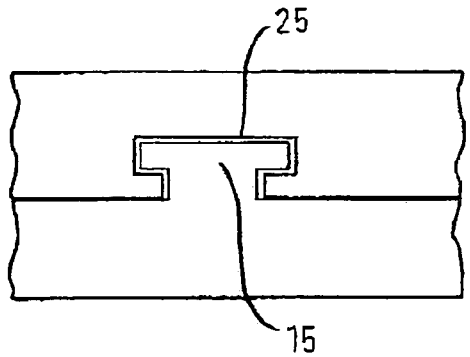
Figure 9C:
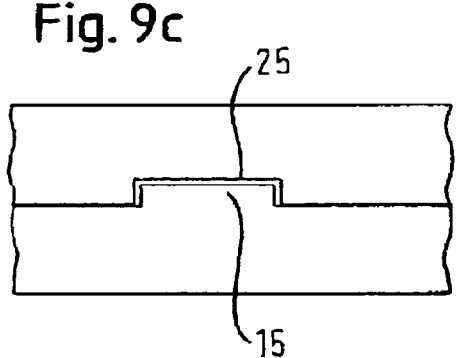
Figure 9D:
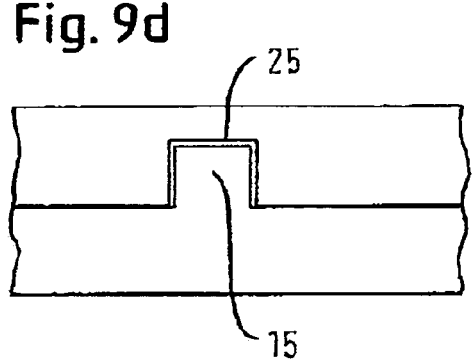
Figure 9E:
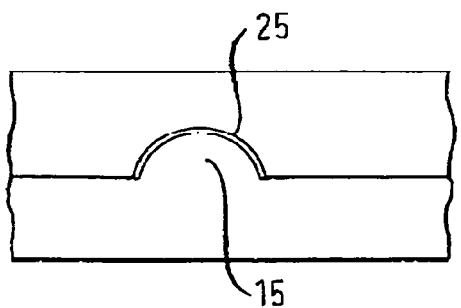

Other modifications within the spirit and scope of the invention also can be made. For example, the cross section of ridge and groove can be T-shaped, rectangular or square in shape, or can be any alternative geometric shape to provide a substantially mating connection for the guide surfaces. FIGS. 9a) to e) show examples of cross sections, like dove-tail shape (FIG. 9a), T-shape (FIG. 9b), rectangular shape (FIG. 9c) and square shape (FIG. 9d) or semicircular shape (FIG. 9e). Further, the cross sectional shape of the groove does not have to be exactly the same as that of the ridge, as long as the grove cross section receives the ridge cross section in a manner that provides a mating connection to enable the two parts to slide relative to each other. In a further modification, the connection between ridge and groove is not provided as a section of a screw or helical line, but is provided to be straight.

In yet a further modification, at least one of the two parts is hollow in the interior and comprises orifices in the base surface or the side wall to allow filling with bone material and/or ingrowth of bone material.

Figure 10:
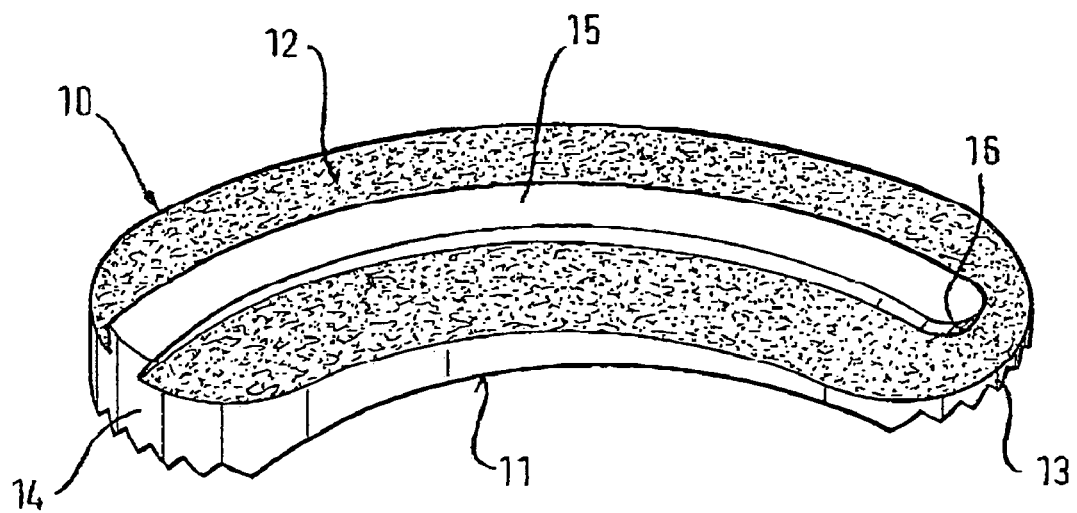
FIG. 10 shows a further modification of the intervertebral implant.

In a further modification, the contact surfaces of the first and/or second part are roughened and/or milled to be step-like as shown in FIG. 10.

In a yet another modification, the outer shape (top view) of the first and/or second part are each straight and not shaped as an arc, curve or segment of a helix. It is possible to make the first and second part exactly the same, wherein the part has both a ridge and a groove. Alternatively the first and second contact surfaces can be shaped like an arc, curve or segment of a helix. Thus, the implant can be made from two like parts.

Figure 11A:
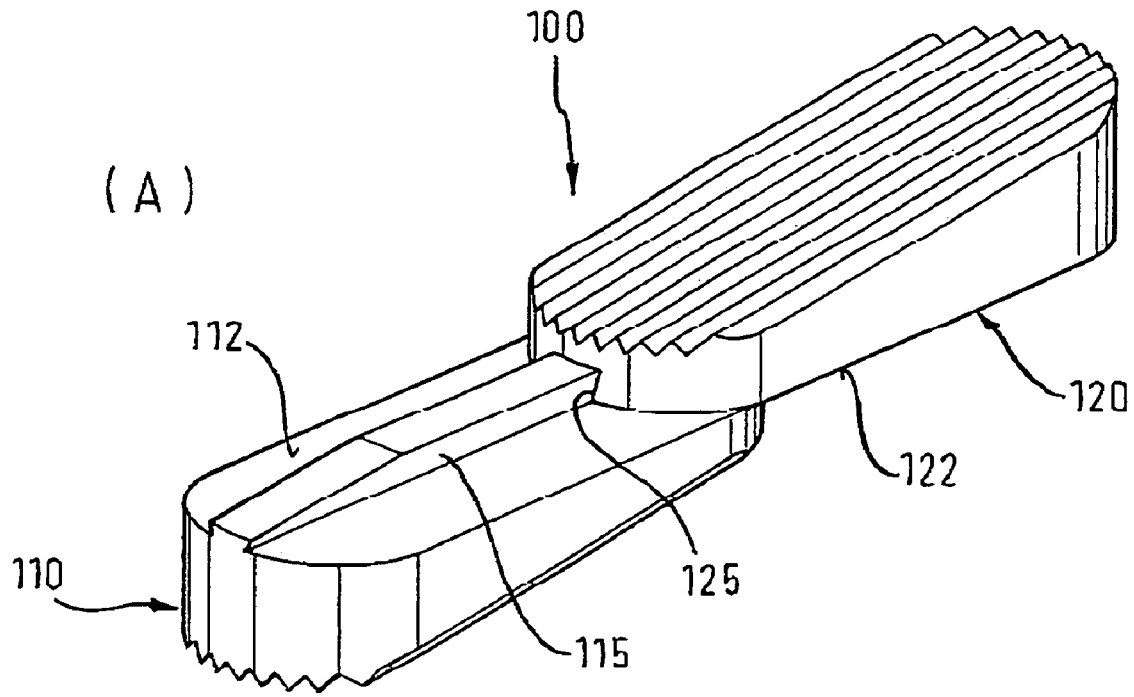
FIG. 11a to 11b show a still further modification of the intervertebral implant.
Figure 11B:
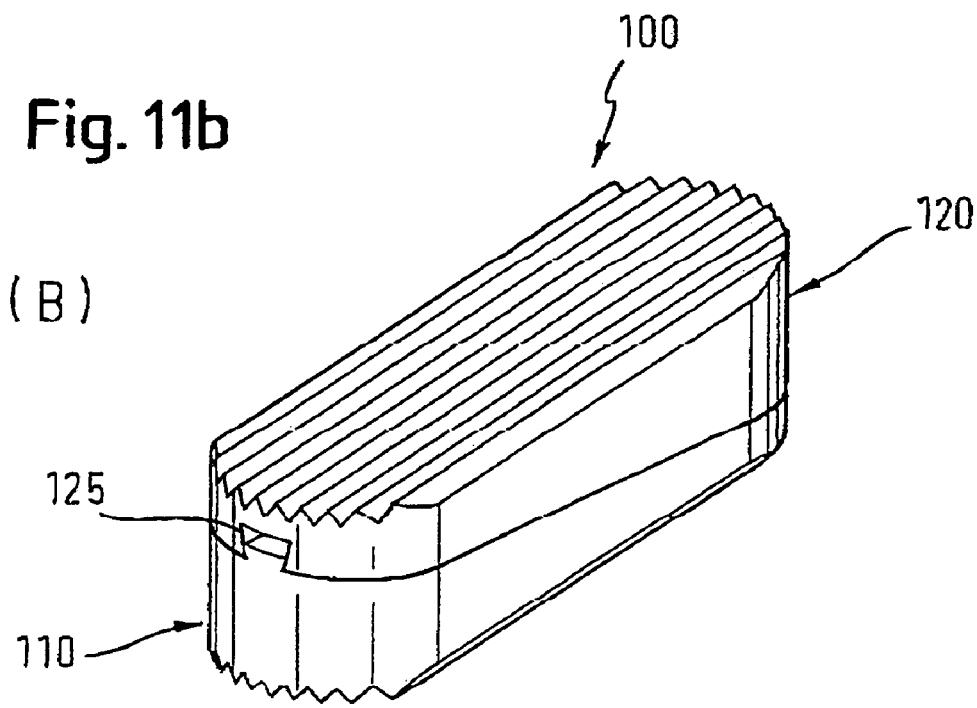

FIG. 11ashows an intervertebral implant 100 comprising two straight, wedge-shaped parts 110, 120 in a first state (A) in which the two parts are minimally engaged. Like in the first embodiment, the parts have corresponding ridge 115 and groove 125 and guide surfaces 112, 122. FIG. 11b shows the implant in a state (B) where the two parts are fully engaged.

In yet a further modification, the base surfaces of the first part and/or second part are provided without grooves.

The embodiments described above and shown herein are illustrative and not restrictive. The scope of the invention is indicated by the claims rather than by the foregoing description and attached drawings. The invention may be embodied in other specific forms without departing from the spirit of the invention. Accordingly, these and other changes which come within the scope of the claims are intended to be embraced therein.

What is claimed is:

1. An intervertebral implant comprising:

a first part having a first end, a second end, a first contact surface provided between the first and second ends, a first guide surface fixed to the first contact surface and extending out from the first contact surface, and a first base surface opposite to said first contact surface;

a second part having a third end, a fourth end, a second contact surface provided between the third and fourth ends, a second guide surface fixed to the second contact surface and recessed into the second contact surface, and a second base surface opposite to said second contact surface;

the first guide surface and the second guide surface comprising cooperating structures so that the first contact surface of the first part can slide relative to the second contact surface of the second part with a translation motion guided by the cooperating structures of the first and second guide surfaces;

wherein the first contact surface is slidable relative to the second contact surface between a first position wherein the first end of the first part is connected with the third end of the second part and a second position wherein the first end of the first part is connected with the fourth end of the second part; and wherein a distance between the first base surface and the second base surface continuously increases while the first base surface remains generally parallel with the second base surface as the first contact surface slides relative to the second contact surface from the first position to the second position.

2. The intervertebral implant according to claim 1, wherein a first plane parallel to said first contact surface intersects a second plane parallel to said first base surface forming an inclination angle of contact $\alpha$; and wherein a third plane parallel to said second contact surface intersects a fourth plane parallel to said second base surface forming an inclination angle of contact $\alpha$.

3. The intervertebral implant according to claim 2, wherein said implant comprises a material and said angle a is determined based on the material and the surface properties of the first and second contact surfaces such that a self-locking mechanism between the first part and the second part is effected.

4. The intervertebral implant according to claim 3, wherein the ridge comprises a first cross-section and the groove comprises a second cross-section, the first cross-section comprising a shape selected from the group comprising a dovetail-shape, a T-shape, a rectangle, a square or a semicircle, and the second cross-section comprises a complementary shape to the first cross-section shape such that the ridge and groove cooperate.

5. The intervertebral implant according to claim 1, wherein the first and second contact surfaces and the first and second guide surfaces comprise an arcuate shape.

6. The intervertebral implant according to claim 1, wherein said first and second parts are straight.

7. The intervertebral implant according to claim 1, further comprising a terminal stop.

8. The intervertebral implant according to claim 1, wherein one of the first guide surface and the second guide surface comprises a ridge and the other of the first guide surface and the second guide surface comprises a groove.

9. The intervertebral implant according to claim 8, wherein the first and second contact surfaces, the ridge and the groove each comprise an arcuate shape.

10. The intervertebral implant according to claim 8, wherein the groove is located in the second contact surface and extends from the third end to a pre-set distance from the fourth end of the second contact surface, thereby providing a terminal stop.

11. The intervertebral implant according to claim 1, said implant further comprising an orifice or a recess.

12. The intervertebral implant according to claim 1, wherein the first contact surface and/or the second contact surface comprise a roughened surface or a step-like surface.

13. The intervertebral implant according to claim 1, wherein the first part comprises a first base surface and the second part comprises a second base surface, wherein at least one of first and second base surfaces comprise groove-shaped recesses.

14. The intervertebral implant according to claim 1, wherein said first part and said second part are formed from a polymer.

15. The intervertebral implant according to claim 14, wherein said polymer is polyetheretherketone.

16. The intervertebral implant according to claim 14, wherein said polymer is polytetrafluoroethylene.

17. The intervertebral implant according to claim 1, wherein said first and second part are formed from a body compatible metal or metal alloy.

* * * * *

UNITED STATES PATENT AND TRADEMARK OFFICE
CERTIFICATE OF CORRECTION

PATENT NO. : 7,618,458 B2  Page 1 of 1
APPLICATION NO. : 11/009224
DATED : November 17, 2009
INVENTOR(S) : Biedermann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 428 days.

Signed and Sealed this

Twenty-sixth Day of October, 2010

David J. Kappos
*Director of the United States Patent and Trademark Office*